(12) United States Patent  (10) Patent No.: US 6,869,593 B2
Frangioni  (45) Date of Patent: Mar. 22, 2005

(54) NON-ISOTOPIC DETECTION OF OSTEOBLASTIC ACTIVITY IN VIVO USING MODIFIED BISPHOSPHONATES

(75) Inventor: John V. Frangioni, Wayland, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 10/424,572

(22) Filed: Apr. 25, 2003

(65) Prior Publication Data

US 2004/0028611 A1 Feb. 12, 2004

Related U.S. Application Data

(63) Continuation of application No. PCT/US01/51312, filed on Oct. 29, 2001.
(60) Provisional application No. 60/244,020, filed on Oct. 27, 2000.

(51) Int. Cl.$^7$ .............................. C07F 9/38; A61K 49/00
(52) U.S. Cl. ........................................ 424/9.6; 548/414
(58) Field of Search ............................ 548/414; 424/9.6

(56) References Cited

U.S. PATENT DOCUMENTS

| 5,453,505 A | 9/1995 | Lee et al. |
| 6,027,709 A | 2/2000 | Little et al. |

FOREIGN PATENT DOCUMENTS

| WO | WO 96/17628 A1 | 6/1996 |
| WO | WO 98/22146 A3 | 3/1998 |
| WO | WO 98/22146 A2 | 3/1998 |
| WO | WO 98/48838 A1 | 11/1998 |
| WO | WO 98/48846 A1 | 11/1998 |
| WO | WO 00/16810 A1 | 3/2000 |

OTHER PUBLICATIONS

Flesch et al., Journal of Chromatography, 489(2), 446–451, 1989.*

Altkorn, D., and Vokes, T., "Treatment of Postmenopausal Osteoporosis," *JAMA*, 285(11):1415–1418, (2001).

Caesar, J., et al., "The Use of Indocyanin Green in the Measurement of Hepatic Blood Flow as a Test of Hepatic Function," *Clin. Sci.*, 21:43–57, (1961).

Chance, B., "Near–Infrared Images Using Continuous, Phase–Modulated, and Pulsed Light with Quantitation of Blood and Blood Oxygenation," *Annals of The New York Academy of Sciences*, 838: 29–45, (1998).

Devoisselle, J.M., et al., "Measurement of In Vivo Tumorous/Normal pH Localized Spectroscopy Using a Fluorescent Marker," *Optical Engineering*, 32(2):239–243, (1993).

Eastell, R., "Treatment of Postmenopausal Osteoporosis," *The New England Journal of Medicine*, 338(11):736–746, (1998).

Farkas, D.L., et al., "Non–Invasive Image Acquisition and Advanced Processing in Optical Bioimaging," *Computerized Medical Imaging and Graphics*, 22:89–102, (1998).

Fujisaki, J., et al., "Osteotropic Drug Delivery System (ODDS) Based on Biophosphonic Prodrug. I: Synthesis and In Vivo Characterization of Osteotropic Carboxyfluorescein," *Journal of Drug Targeting*, 3:273–282, (1995).

Fujisaki, J., et al., "Osteotropic Drug Delivery System (ODDS) Based on Biophosphonic Prodrug. III: Pharmacokinetics and Targeting Characteristics of Osteotropic Carboxyfluorescein," *Journal of Drug Targeting* 4:117–123, (1996).

Fujisaki, J., et al., "Physicochemical Characterization of Biophosphonic Carboxyfluorescein for Osteotropic Drug Delivery," *J. Pharm. Pharmacol.*, 48:798–800, (1996).

Fujisaki, J., et al., "Osteotropic Drug Delivery System (ODDS) Based on Biophosphonic Prodrug. IV Effects of Osteotropic Estradiol on Bone Mineral Density and Uterine Weight in Ovariectomized Rats;" *Journal of Drug Targeting*, 5(2):129–138, (1997).

Fujisaki, J., et al., "Osteotropic Drug Delivery System (ODDS) Based on Biophosphonic Prodrug. V. Biological Disposition and Targeting Characteristics of Osteotropic Estradiol," *Biol. Pharm. Bull.*, 20(11):1183–1187, (1997).

Glorieux, F.H., et al., "Cyclic Administration of Pamidronate in Children With Severe Osteogenesis Imperfecta," *The New England Journal of Medicine*, 339(14):947–952, (1998).

He, Y.L., et al., "Measurement of Blood Volume Using Indocyanine Green Measured with Pulse–Spectrophotometry: Its Reproducibility and Reliability," *Crit. Care Med.*, 26(8):1446–1451, (1998).

Hirabayashi, H., et al., "Bone–Specific Delivery and Sustained Release of Diclofenac, A Non–Steroidal Anti–Inflammatory Drug, Via Bisphosphonic Prodrug Based on the Osteotropic Drug Delivery System (ODDS)," *Journal of Controlled Release*, 70:183–191, (2001).

Karrar, S., et al., "Photochemotherapie Kutaner Rektumkarzinom–Metastasen mit Idocyaningrün," *Deutsche Medizinische Wochenschrift*, 122:1111–1114, (1997).

Klenner, T., et al., "Anticancer–Agent–Linked Phosphonates with Antiosteolytic and Antineoplastic Properties: A Promising Perspective in the Treatment of Bone–Related Malignancies?," *J. Cancer Res. Clin. Oncol.*, 116:341–350, (1990).

(List continued on next page.)

Primary Examiner—Fiona T. Powers
(74) Attorney, Agent, or Firm—Hamilton, Brook, Smith & Reynolds, P.C.

(57) ABSTRACT

The present invention is directed to a non-isotopic methods for the in vitro and in vivo detection of hydroxyapatite-positive cells and structures.

27 Claims, 7 Drawing Sheets

OTHER PUBLICATIONS

Lin, J.H., et al., "Physiological Disposition of Alendronate, A Potent Anti–Osteolytic Bisphosphonate, In Labratory Animals," *Drug Metabolism and Disposition*, 19(5):926–932, (1991).

Mahmood, U., et al., "Near–Infrared Optical Imaging of Protease Activity for Tumor Detection," *Radiology*, 213:866–870, (1999).

Martin, M.B., et al., "Bisphosphonates Inhibit the Growth of *Trypanosoma brucei, Trypanosoma cruzi, Leishmania donovani, Toxoplasma gondii*, and *Plasmodium faciparum*: A Potential Route to Chemotherapy," *J. Med. Chem.*, 44:909–916, (2001).

Mujumdar, R.B., et al., "Cyanine Dye Labeling Reagents: Sulfoindocyanine Succinimidyl Esters," *Bioconjugate Chemistry*, 4(2):105–111, (1993).

Mundy, G.R. and Yoneda, T., "Bisphosphonates as Anticancer Drugs," *The New England Journal of Medicine*, 339(6):398–400, (1998).

Ntziachristos, V., et al., "Concurrent MRI and Diffuse Optical Tomography of Breast After Indocyanine Green Enhancement," *PNAS*, 97(6):2767–2772, (2000).

Quaresima, V., et al., "Identification and Quantification of Intrinsic Optical Contrast for Near–Infrared Mammography," *Photochemistry and Photobiology*, 67(1):4–14, (1998).

Rockson, S.G., et al., "Photoangioplasty for Human Peripheral Atherosclerosis Results of a Phase I Trial of Photodynamic Therapy With Motexafin Lutetium (Antrin)," *Circulation*, 102:2322–2324, (2000).

Rogers, M.J., et al., "Cellular and Molecular Mechanisms of Action of Bisphosphonates," *Cancer (Supplement)*, 88(12):2961–2978, (2000).

Zaheer, A., et al., "Near–Infrared Fluorescence Imaging of Osteoblastic Activity," *Proc. Am. Assoc. Cancer Res. Ann.* 42:483 (2001); 92$^{nd}$ Annual Meeting of the American Association for Cancer Research; New Orleans, LA, USA (Mar. 24–28, 2001): Abstract No. 2602.

* cited by examiner

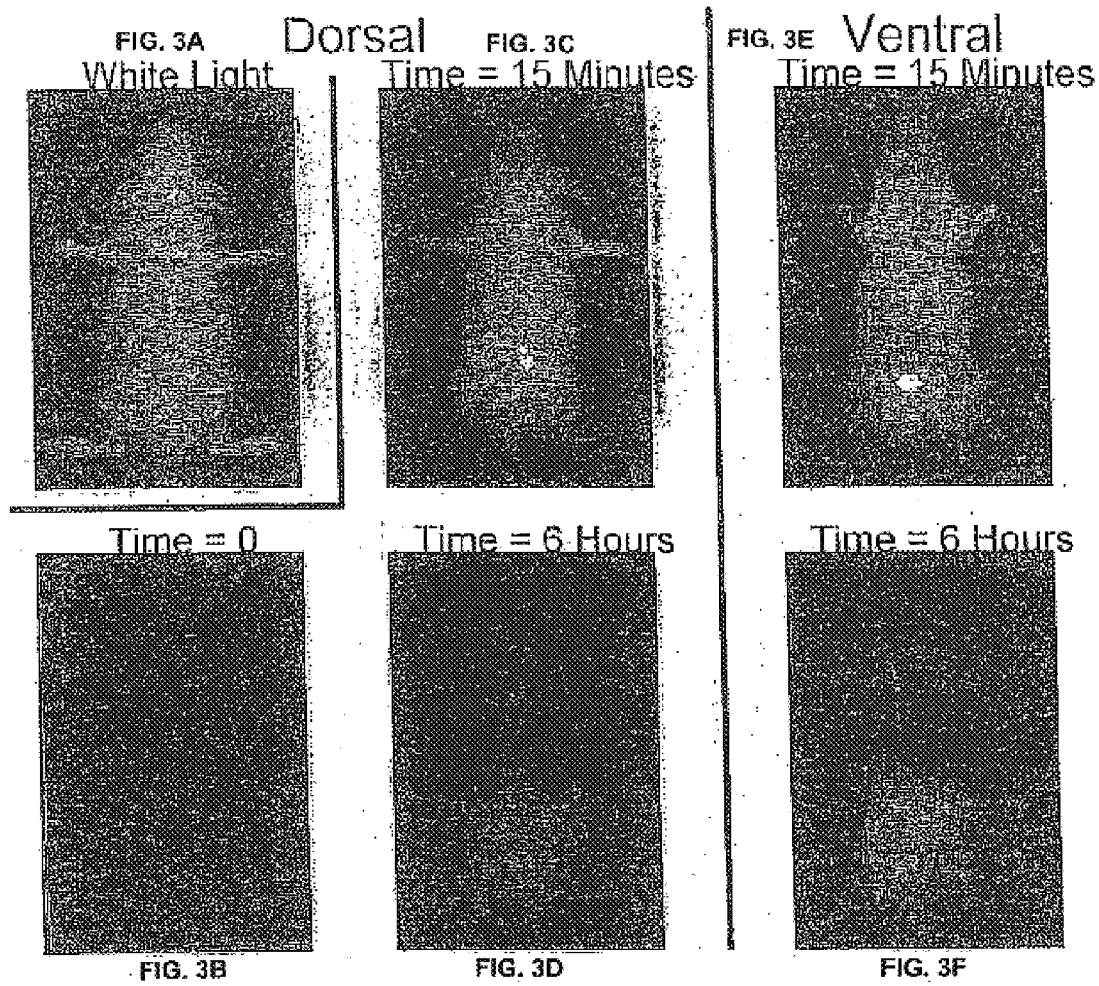

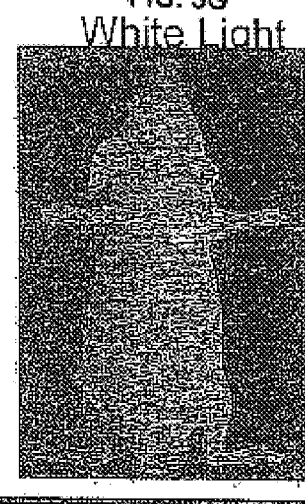
FIG. 3G White Light
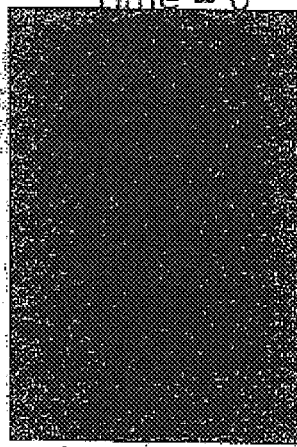
FIG. 3H Time = 0
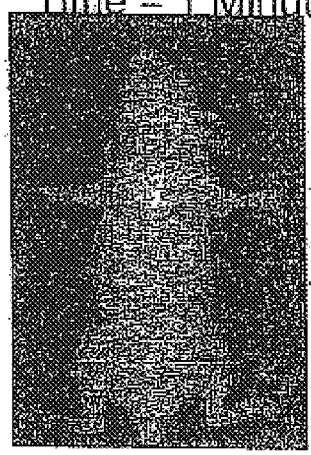
FIG. 3I Time = 1 Minute
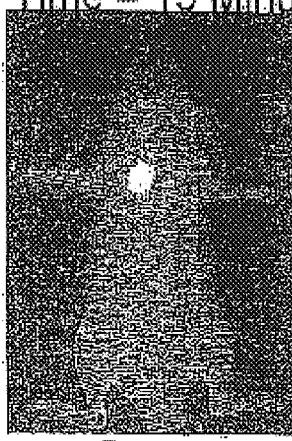
FIG. 3J Time = 15 Minutes
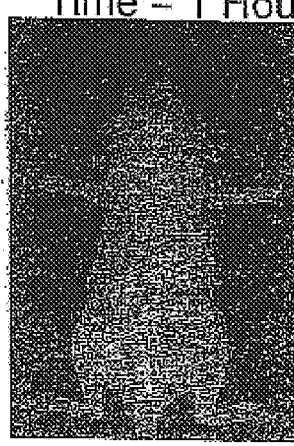
FIG. 3K Time = 1 Hour
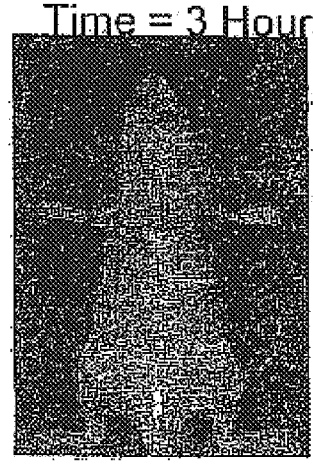
FIG. 3L Time = 3 Hours

NON-ISOTOPIC DETECTION OF OSTEOBLASTIC ACTIVITY IN VIVO USING MODIFIED BISPHOSPHONATES

RELATED APPLICATIONS

This is a Continuation of International Application No. PCT/US01/51312, which designated the United States and was filed Oct. 29, 2001, published in English, which claims the benefit of U.S. Provisional Application No. 60/244,020, filed Oct. 27, 2000, the entire teachings of which are incorporated herein by reference.

BACKGROUND OF THE INVENTION

The development and maintenance of the vertebral skeleton is a complex process, but in simplest terms represents a balance between osteoblast-induced mineralization and osteoclast-induced demineralization. Osteoblast-like cells are also present in the vascular wall and participate in the earliest manifestations of atherosclerosis. Hydroxyapatite (HA; $Ca_{10}(PO_4)_6(OH)_2$, also know as hydroxylapatite) is the major mineral product of osteoblasts and calcifying vascular cells and binds naturally occurring pyrophosphates and phosphonates with high affinity. Osteoblastic activity occurs at sites of new bone formation, i.e., sites of deposition of hydroxyapatite. New bone formation occurs after fracture, at sites of bony infections, and especially at the sites of certain cancer metastases (e.g., prostate cancer metastases).

At the present time, osteoblastic activity is detected in vivo using radionuclides and SPECT imaging. For instance, a common technique is the "bone scan", which utilizes the radiometal $^{99m}$Tc coupled to the bisphosphonate compound methylene bisphosphonate (MDP). Unfortunately, radioscintigraphic detection does not provide high-resolution anatomical detail, and requires the use of radioactive compounds.

Fluorescence imaging is found at the heart of numerous chemical and biomedical analysis schemes. Many of these schemes are based on the introduction of a fluorescent species as a marker, stain, dye or indicator (Devoisselle et al. (1993) *Optical Engineering* 32:239; Haugland and Minta, "Design and Application of Indicator Dyes," Noninvasive Techniques in Cell Biol., ed. B. H. Satir, Chap: 1, p 1, (Wiley-Liss, New York, N.Y., 1990); Gross, "Quantitative Single Cell Fluorescence Imaging of Indicator Dyes," Noninvasive Techniques in Cell Biol., ed. B. H. Satir, Chap. 2, p 21, (Wiley-Liss, New York, N.Y., 1990). To date, however there has not been a non-isotopic method for directly detecting HA in vivo.

It is an object of the present invention to use bisphosphonate compounds for use in non-isotopic (i.e., without the need for radioactivity) detection of hydroxyapatite, such as to determine osteoblastic activity in vivo.

SUMMARY OF THE INVENTION

One aspect of the present invention provides a contrast agent represented in the general formula [I] or pharmaceutically acceptable salts thereof:

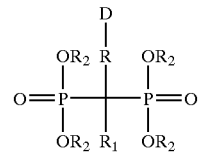

wherein

D represents a fluorescent moiety;

R represents a linking group that covalently links the dye (D) and bisphosphonate moiety;

$R_1$ represents H, —OH, or a halogen; and $R_2$ represents, independently for each occurrence, a free electron pair, hydrogen, or a pharmaceutically acceptable counterion.

In certain embodiments, R is an amine substituted loweralkyl which forms an amide bond with a pendant group of the fluorescent moiety, e.g., such as —$(CH_2)_L$—NH—, where L is an integer from 1 to 6.

In certain embodiments, $R_1$ is —OH or —Cl.

In certain embodiments, D is near-infrared fluorescent moiety., e.g., a near-infrared fluorescent dye.

In certain embodiments, D is a polysulfonated indocyamine dye.

In certain embodiments, the fluorescent moiety is represented by the formula [II]:

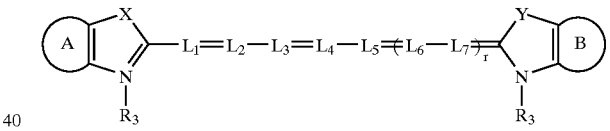

wherein $L_1$–$L_7$ are each, independently, a substituted or unsubstituted methine, provided that one of $L_1$–$L_7$ is substituted with the linker group R which is attached to the bisphosphonate;

$R_3$, independently for each occurrence, is a substituted or unsubstituted alkyl;

A and B are each, independently, 5–7 membered substituted or unsubstituted aromatic rings;

X and Y are the same or different and each is a group of the formula —O—, —S—, —CH=CH— or —$C(R_4)_2$—;

$R_4$, independently for each occurrence, is a hydrogen or substituted or unsubstituted lower alkyl; and r is 0, 1 or 2.

For example, fluorescent moiety [II] can have one or more of the following features: (a) is free of a carboxylic acid group in a molecule; (b) r is 1; (c) includes 4 or more sulfonic acid groups; (d) includes 10 or less sulfonic acid groups; (e) A and B are, independently, benzo or naphtho rings; and (f) X and Y are —$C(CH_3)_2$—.

In certain embodiments, the fluorescent moiety is represented by the formula

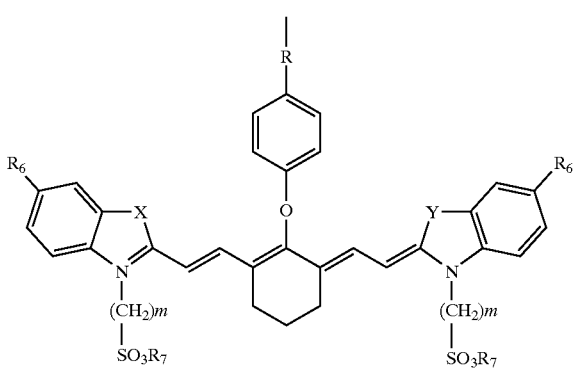

wherein

X and Y are the same or different and each is a group of the formula —O—, —S—, —CH=CH— or —C(R$_4$)$_2$—;

R$_4$, independently for each occurrence, is a hydrogen or substituted or unsubstituted lower alkyl; and R$_6$, independently for each occurrence, is hydrogen or —SO$_3$R$_7$;

R$_7$, independently for each occurrence, is hydrogen or a pharmaceutically acceptable counter ion;

m is 0, 1, 2, 3, 4 or 5.

In many preferred embodiments, the fluorescent moiety is a near-infrared fluorescent moiety and has an extinction coefficient of at least 50,000 M$^{-1}$cm$^{-1}$ in aqueous medium, and even more preferably at least 100,000, 200,000 or even 300,000 M$^{-1}$cm$^{-1}$.

In many preferred embodiments, the fluorescent moiety is a near-infrared fluorescent moiety and has a quantum efficiency, $\Phi_F$, of at least 25%, and even more preferably at least 30%, or even 40%.

In preferred embodiments, the contrast agent has an LD$_{50}$ of 50 mg/Kg or greater humans, and even more preferably of at least 100, 250 or even 500 mg/Kg.

In preferred embodiments, the contrast agent has a half-life in the human body of at least 10 minutes, and even more preferably at least 20, 30 or even 45 minutes.

Another aspect of the invention provides a contrast agent comprising a bisphosphonate covalently linked to a near-infrared fluorescent moiety, wherein the contrast agent (a) has an extinction coefficient of at least 100,000 M$^{-1}$cm$^{-1}$ in aqueous medium, (b) has an LD$_{50}$ of at least 100 mg/Kg in humans, and (c) has a half-life in the human body of at least 10 minutes.

In certain embodiments, the bisphosphonate is selected from the group consisting of alendronate, clodronate, EB-1053, etidronate, ibandronate, incadronate, neridronate, olpadronate, phosphonate, pamidronate, risedronate, tiludronate, YH 529 and zonledronate.

Yet another aspect of the present invention provides methods for manufacturing a composition of for in vivo imaging by formulating a contrast agent described herein in a pharmaceutically acceptable excipient.

Still another aspect of the invention provides a kit for in vivo imaging comprising a contrast agent of the invention in association with instructions for administering the contrast agent to a patient.

Another aspect of the invention provides a method for in vivo imaging of tissue with exposed hydroxyapatite, comprising, (i) administering to the animal a contrast agent of any of claims 1–16 in an amount sufficient to render hydroxyapatite-containing tissue detectable by a fluorescent detector;

(ii) obtaining a fluorescent image of the animal, or at least a portion thereof, at a wave length(s) which detects the contrast agent;

(iii) constructing an image of the animal including the pattern of distribution of the contrast agent.

The subject method can be used for evaluating a bone for its condition and/or biomechanical property, e.g., for determining bone matrix density and/or detecting changes in bone matrix volume. For instance, the method can be used as part of a protocol for diagnosing osteoporosis. In other embodiments, the method can be used for determining at least one of anisotropic elastic constants, bone strength, or fracture risk.

The subject method can also be used for diagnostic detection of bone diseases accompanied with abnormality of calcium hydroxyapatite, such as for detecting the presence of osteoblastic metastase.

Another embodiment of the method can be used for detecting of vessel micro-calcification, such in the detection of sub-clinical vessel calcification, e.g., as a way of more accurately assigning cardiovascular risk, as well as an adjunct to standard catheterization procedures, or as a prognostic tool to assess cardiovascular risk.

Figure 1A:
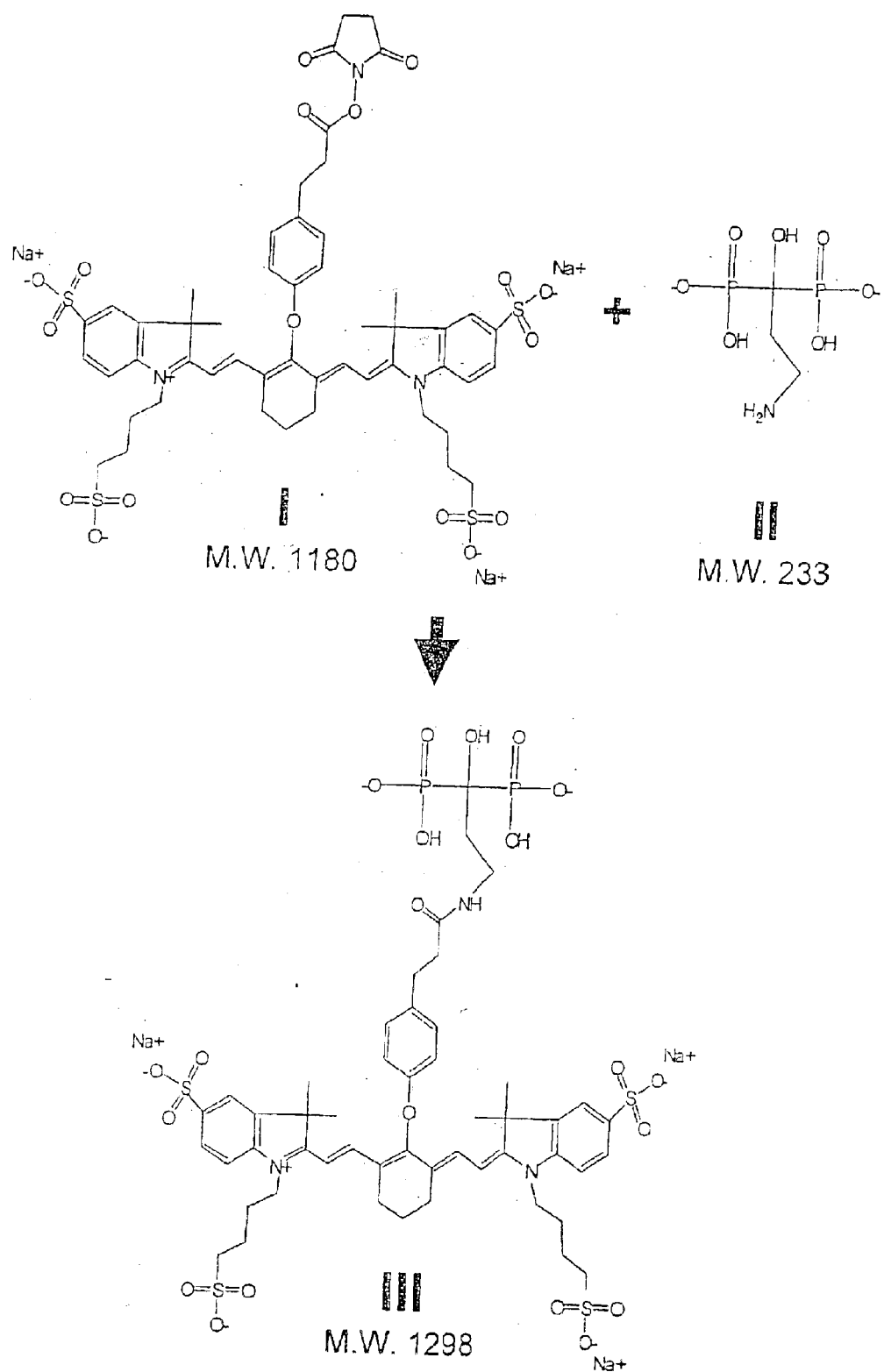
FIG. 1: Conjugation of Pamidronate to IRDye78, Purification of the Product and Spectral Characteristics.

A. The primary amine of pamidronate disodium (I) was conjugated to the sodium salt of the N-hydroxysuccinimide (NHS) ester of IRDye78 (II), as described in the Experimental Protocol, yielding the NIR fluorescent product pamidronate/IRDye78 (III; Pam78). The chemical structure and molecular weight (M.W.) for each compound at pH 7.4 is shown. The carboxylic acid of IRDye78 is compound I with a hydrogen replacing the succinimide group.

B. The reactants and products of the chemical reaction described in FIG. 1A were separated using thin-layer chromatography (TLC) as described in the Experimental Protocol, An actual TLC plate representative of this procedure is shown. The carboxylic acid of IRDye78 (Lane 1; arrowhead), free pamidronate (Lane 2; closed arrow; visualized with ninhydrin as described in the Experimental Protocol) and Pam78 (Lane 3; open arrow) separated with R$_f$ values of 0.8, 0, and 0.6, respectively. The origin is indicated, and the mobile phase front is shown across the top of the plate as a dashed line.

C. Absorbance wavelength scans using IRDye78 (left panel) and Pam78 (right panel) at a concentration of 1 µM in NK buffer. The wavelength of peak absorption is indicated.

D. Excitation/emission fluorescence wavelength scans using IRDye78 (left panel) and Pam78 (right panel) at a concentration of 500 nM in NK buffer. For fluorescence excitation scans (solid lines), emission wavelength was fixed at 796 nm. For fluorescence emission scans (dashed lines), excitation wavelength was fixed at 771 nm. The peak wavelength for each scan is shown above the corresponding curve.

FIG. 2: Hydroxyapatite Binding Properties of IRDye78 and Pam78:

A. The kinetics of binding to hydroxyapatite (HA) crystals was measured for Pam78 (solid circles) and the carboxylic acid of IRDye78 (IRDye78 alone; open circles), as described in the Experimental Protocol.

Measurements were acquired at 5, 15, and 30 minutes, and 1, 2, 3, and 24 hours after mixing. On the ordinate is shown the number of μmol of each compound bound per gram of HA (mean±SEM).

B. Steady state binding to HA crystals was measured for Pam78 (solid bars) and the carboxylic acid of IRDye78 (IRDye78 alone; open bars), as described in the Experimental Protocol. On the abscissa is the concentration of applied compound. On the ordinate is shown the number of μmol of each compound bound per gram of HA (mean±SEM) at 3 hours.

C. Competition of Pam78 binding to HA using unlabeled pamidronate was performed as described in the Experimental Protocol. On the ordinate is shown the number of μmol of each compound bound per gram of HA (mean±SEM) relative to binding of Pam78 in the absence of unlabeled pamidronate.

D. Direct visualization of Pam78 binding to HA was accomplished using NIR fluorescence microscopy as described in the Experimental Protocol. Phase contrast (left panels) and NIR fluorescence images (right panels) of HA crystals treated with 1 μM Pam78 (top panels) or the carboxylic acid of IRDye78 (bottom panels) are shown.

Figure 3N:
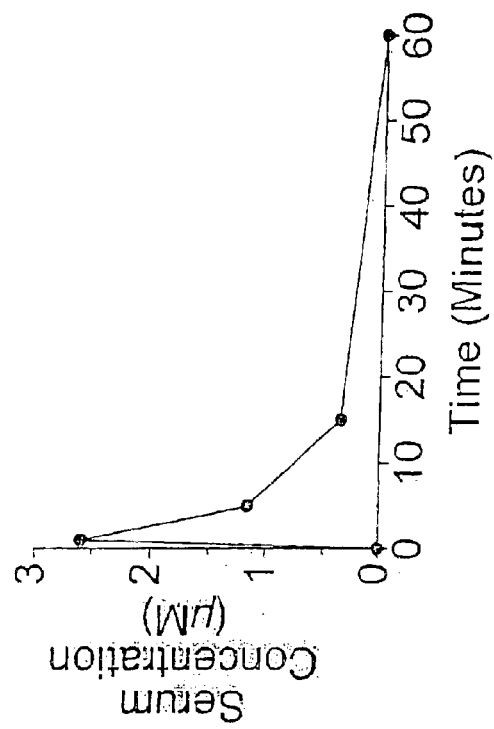
Figure 3M:
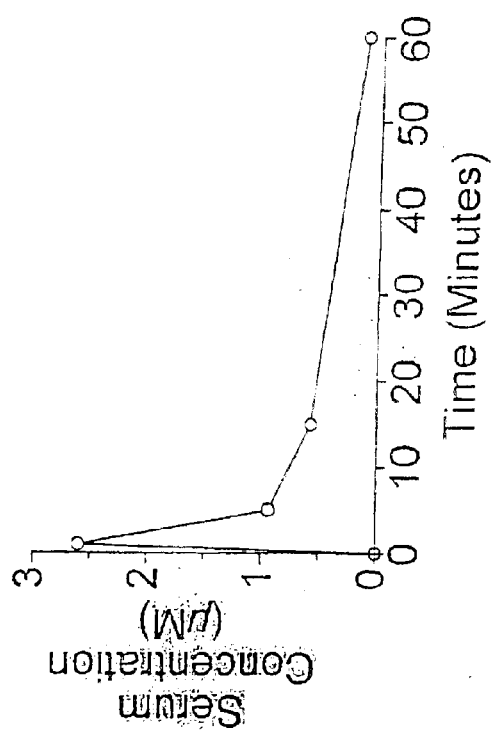
Figure 4A:
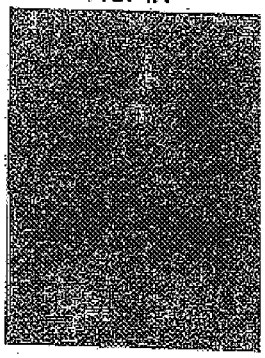
Figure 4B:
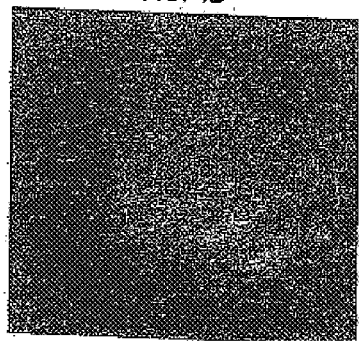
Figure 4C:
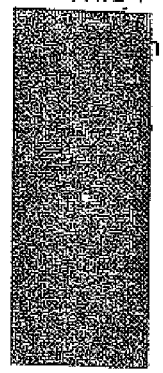
Figure 4D:
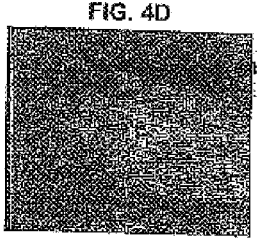
Figure 4E:

FIG. 3: In Vivo Biodistribution and Pharmacokinetics of IRDye78 and Pam78 using Near-Infrared Fluorescence Imaging:

A–F. 2.6 nmol of IRDye78 carboxylic acid in 80 μl of PBS was injected intravenously in the tail vein of a hairless (nu/nu) mouse and imaged with the small animal imaging system as described in the Experimental Protocol. The left photographs (FIGS. 3A–D) show dorsal images and the right photographs (FIGS. 3E–F) show ventral images of the same mouse. For orientation, a white light image and calibration bar are shown in the top left photograph (FIG. 3A). All NIR fluorescence images were acquired using a 500 msec exposure time and are normalized to the 15 minute image. The Time=0 photograph (FIG. 3B) shows NIR autofluorescence prior to compound injection. Dorsal and ventral images at 15 minutes (FIG. 3C) and six hours (FIG. 3D) post-injection are shown. In the 15 minute dorsal image (FIG. 3C), note is made of sub-millimeter skin defects (D) which appear highlighted after injection. In the 15 minute ventral image (FIG. 3C), note is made of intense signal in the bladder (B). In the six hour ventral image (FIG. 3D), note is made of signal emanating from loops of the large (LI and small (SI.

G–L. 2.6 nmol of Pam78 in 80 μl of PBS was injected intravenously in the tail vein of a hairless (nu/nu) mouse and dorsal images were obtained with the small animal imaging system described in the Experimental Protocol. For orientation, a white light image and calibration bar are shown in the top left photograph (FIG. 3G). All NIR fluorescence images were acquired using a 500 msec exposure time and are normalized. The Time=0 image (FIG. 3H) shows NIR autofluorescence prior to compound injection. As the injected fluorophore is cleared, areas of high HA in the skeleton become visible. As early as 15 minutes after injection, ribs (R), spine (Sp) and are visualized (FIG. 3J). Signal emanating from the kidneys is also indicated (K). By 3 hours, the phalanges (P), wrist (W), skull (Sk), pelvis (Pe), femur (F) and ankle (A) become visible (FIG. 3L).

M–N. Serum concentration of IRDye78 carboxylic acid (left panel (FIG. 3M); open circles) and Pam78 (right panel (FIG. 3N); closed circles) were measured as detailed in the Experimental Protocol after intravenous injection of 2.6 nmol of each compound into the tail vein. Ordinate shows serum concentration as measured spectrophotometrically. Abscissa shows time in minutes.

FIG. 4: High Resolution In Vivo Near-Infrared Fluorescence Imaging of HA: Specific anatomic sites of the same living animal shown in FIGS. 3G–L were imaged six hours post injection of Pam78 using the zoom lens capability of the small animal imaging system described in the Experimental Protocol. Images were normalized for optimal appearance of each bony structure. For orientation, calibration bars are shown in each photograph:

FIG. 4: High Resolution In Vivo Near-Infrared Fluorescence Imaging of HA: Specific anatomic sites of the same living animal shown in FIGS. 3G–L were imaged six hours post injection of Pam78 using the zoom lens capability of the small animal imaging system described in the Experimental Protocol. Images were normalized for optimal appearance of each bony structure. For orientation, calibration bars are shown in each photograph:

A. Ventral image of the head showing intense staining of the nasal bone (Na) and maxilla (Mx). The anterior palatine foramen (APF) is also visible, as is the (out of focus) mandible (Ma).

B. Oblique image of rib cage showing costochrondral junction (arrow; CCJ).

C. The thoracic spine showing spinous (SP) and transverse processes (TP).

D. The front paw showing individual phalanges (P). Note is made of small opaque hairs (H) near the wrist preventing penetration of NIR light.

E. The mid-tail showing caudal vertebrae (CV). Soft tissue and skin overlying these bones can be seen as a superimposed ribbed and checkered pattern.

BEST MODE FOR CARRYING OUT THE INVENTION

I. Overview

In vertebrates, the development and integrity of the skeleton requires hydroxylapatite deposition by osteoblasts. Hydroxylapatite deposition is also a marker of, or a participant in, processes as diverse as cancer and atherosclerosis. Prior to the present invention, sites of exposed hydroxylapatite are imaged in vivo using γ-emitting radioisotopes. The scan times required are long, and the resultant radioscintigraphic images suffer from relatively low resolution.

The present invention provides methods and compositions for improved imaging of tissues which include hydroxyapatite. In particular, the present invention provides fluorescent bisphosphonate derivatives that exhibits rapid and specific binding to hydroxylapatite in vitro and in vivo.

Certain preferred embodiments are directed to the use of bisphosphonates coupled to near-infrared fluorescent dyes to generate contrast agents that retain high affinity and rapid binding to hydroxyapatite. Relative to visible light fluorophores, contrast agents incorporating near-infrared (NIR) fluorophores permit highly sensitive detection of new bone formation, or other hydroxyapatite-positive tissue, with minimal interference from tissue absorbance, autofluorescence, and scatter. In addition to in vitro uses, clinical applications which contemplates include, but are not limited to:

In vivo detection of osteoblastic metastases: The ability to non-isotopically visualize osteoblastic metastases in a living animal, without sacrifice, should permit more rapid and efficient evaluation of anti-tumor therapies.

Histopathological detection of vessel micro-calcification: A new paradigm in atherosclerosis research is that plaque formation has many features of osteoblastosis. The subject contrast agents permit detection of subclinical vessel calcification as a way of more accurately assigning cardiovascular risk.

In vivo detection of vessel micro-calcification: The subject contrast agents can be used to detect vessel micro-calcification, such as for in vivo NIR fluorescent imaging of vessel calcification either as an adjunct to standard catheterization procedures, or as a prognostic tool to assess cardiovascular risk.

II. Exemplary Compounds

The subject compositions include contrast agents generated by the conjugation of a bisphosphonate moiety with a fluorescent moiety, such as an organic dye or fluorescent protein. In preferred embodiments, such contrast agents are represented in the general formula [I], or pharmaceutically acceptable salts thereof:

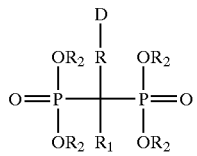

wherein

D represents a fluorescent moiety (also referred to herein as a "dye");

R represents a linking group that covalently links the dye (D) and bisphosphonate moiety;

$R_1$ represents H, —OH, or a halogen; and $R_2$ represents, independently for each occurrence, a free electron pair, hydrogen, or a pharmaceutically acceptable counterion.

A successful bone scanning agent and bone therapy requires high and rapid uptake of the agent in bone with clearance from the blood and soft tissues, such as muscle, of that part of the agent not taken up in the bone.

A. Exemplary Bisphosphonate Moieties

Bisphosphonates are synthetic analogs of naturally occurring inorganic pyrophosphates and have been used for many years in the treatment of Paget's Disease and hypercalcemia because like inorganic pyrophosphates, bisphosphonates bind to hydroxyapatite crystals in mineralized bone matrix, inhibit the recruitment and function of osteoclasts and stimulate osteoblasts to produce an inhibitor of osteoclast formation. Bisphosphonates are resistant to metabolic and enzymatic inactivation by skeletal pyrophosphatases as they contain a phosphorous-carbon-phosphorous backbone rather than the phosphorous-oxygen-phosphorous backbone of pyrophosphates.

Bisphosphonates, pyrophosphates and bisphosphonate-like compounds, collectively referred to herein as "bisphosphonates" are those compounds exhibiting the characteristics of compounds having a phosphate-oxygen-phosphate or phosphate-carbon-phosphate backbone which characteristics comprise the ability to bind strongly calcium crystals and affect osteoclast-mediated bone resorption. As used herein, bisphosphonates include both geminal and non-geminal bisphosphonates. A number of bisphosphonates are commercially available and can be adapted for use in the subject methods and compositions. These include, but are not limited to:

alendronate 4-amino-1-hydroxybutylidene)bis-phosphonate clodronate (dichloromethylene)-bis-phosphonate EB-1053 1-hydroxy(1-pyrrolidinyl)-propylidene)bis-phosphonate etidronate, 1-hydroiyethylylidene)-bisphosphonate ibandronate 1-hydroxy(methylpentylamino)propylidene) bis-phosphonate incadronate [(cycloheptylamino)-methylene]bis-phosphonate neridronate (6-aminohydroxyhexylidene)bis-phosphonate olpadronate ((3-dimethylamino)-1-hydroxypropylidene) bis-phosphonate pamidronate 3-amino-1-hydroxypropylidene)bis-phosphonate)

risedronate (1-hydroxy(3-pyridinyl)-ethylidene)bis-phosphonate tiludronate [[(4-chlorophenyl)thio)-methylene]bis-phosphonate YH 529 (1-hydroxyimidazo-(1,2-a)pyridinylethylidene) bis-phosphonate zoledronate 1-hydroxy-2-(1H-imidazole-1-y)ethylidene) bis-phosphonate In certain embodiments, the bisphosphonate is selected from the group consisting of pyrophosphonates, thiobisphosphonates, and nitrobisphosphonates. "Nitrobisphosphonates" are compounds comprising a nitrogen atom bound to two phosphonate groups. "Thiobisphosphonates" are compounds comprising a sulfur atom bound to two phosphonate groups.

Referring to Formula I above, in certain preferred embodiments, R' is H, —OH or —Cl, and R is an amine substituted alkyl, e.g., —(CH$_2$)$_L$—NH— where L is an integer from 1 to 6, which forms an amide linkage with the dye moiety.

B. Exemplary Fluorescent Moieties

As described in further detail below, fluorescent, and preferably near-infrared detection of hydroxylapatite can be used to study skeletal development, osteoblastic metastasis, coronary atherosclerosis, and other human diseases.

There are a wide range of fluorescent moieties which can be used to form the subject contrast agents. Such moieties include organic dyes as well as fluorescent proteins.

Examples of appropriate dyes include rhodamines, indocyanines, fluoresceins, hematoporphyrins, and fluoresdamines. Examples of fluorescent proteins include phytofluors (plant phytochromo apoproteins) and green fluorescent proteins. Selection of the appropriate fluorescent moiety will also require considering such factors as (i) the ability of the agent to be conjugated to the bisphosphorate moiety without substantially reducing the usefulness of the fluorescent probe (e.g. retains high extinction coefficient and quantum efficiency), (ii) the resulting conjugate is water-soluble, (iii) the resulting conjugate is non-toxic (e.g. has an LD$_{50}$ of 100 mg/Kg or higher, and more preferably greater than 300 mg/K), (iv) the resulting conjugate has a sufficient half-life in the body (e.g., preferably grater than 10 minutes, more preferably greater than 30 minutes).

Although any fluorescent dye may be suitable, dyes that absorb and emit radiation within the near infrared (NTR) region of the electromagnetic spectrum are preferred. Bone exhibits extremely high autofluorescence in the ultraviolet and visible ranges and tissue photon scatter in these ranges precludes imaging of deep structures. In fact, biological tissue exhibits a high photon absorbance in both the visible wavelength range (350–700 nm; secondary to hemoglobin, tissue pigments, etc.) and infrared (>900 nm; secondary to lipids and water). However, in the wavelength range 700 nm to 900 nm (near-infrared; NIR), the absorbance spectra for all bio-molecules reach minima, thus permitting deep photon penetration into tissue (NIR window). The benefits of using NIR fluorescent dyes as labels include.

(1) there is very low interference at the NIR wavelength of about 650 to 1000 nm where only a few classes of compounds exhibit significant absorption or fluorescence, (2) NIR fluorescent dyes are compatible with the use inexpensive gallium-aluminum-arsenide (Ga—Al—As) semiconductor laser diodes to induce fluorescence; and (3) NIR detection permits flexibility in selecting silicon photodetectors.

Compounds that possess absorbance at the lower NIR (700–850 nm), herein "near-infrared fluorescent moieties", include phthalocyanine, indocyanine, and napthalocyanine dyes, metal complex dyes, triphenyl- or diphenylmethanes, azo dyes, quinones, and carbocyanine dyes.

Cyanine dyes with intense absorption and emission in the near-infrared (NIR) region are particularly useful because biological tissues are optically transparent in this region (B. C. Wilson, Optical properties of tissues. Encyclopedia of Human Biology, 1991, 59 587–597). For example, indocyanine green, which absorbs and emits in the NIR region has been used for monitoring cardiac output of hepatic functions, and liver blood flow (Y-L. He, H. Tanigami, H. Ueyama, T. Mashimo, and I. Yoshiya, Measurement of blood volume using indocyanine green measured with pulse-spectrometry: Its reproducibility and reliability. Critical Care Medicine, 1998, 26(8), 1446–1451; J. Caesar, S. Shaldon, L. Chiandussi, et al., The use of Indocyanine green in the measurement of hepatic blood flow and as a test of hepatic function. Clin. Sci. 1961, 21, 43–57) and its functionalized derivatives have been used to conjugate biomolecules for diagnostic purposes (R. B. Mujumdar, L. A. Ernst, S. R. Mujumdar, et al., Cyanine dye labeling reagents: Sulfoindocyaninesuccinimidyl esters. Bioconjugate Chemistry, 1993, 4(2), 105-1 1 1; Linda G. Lee and Sam L. Woo. "N-Heteroaromatic ion and iminium ion substituted cyanine dyes for use as fluorescent labels", U.S. Pat. No. 5,453,505; Eric Hohenschuh, et al. "Light imaging contrast agents", WO 98/48846; Jonathan Turner, et al. "Optical diagnostic agents for the diagnosis of neurodegenerative diseases by means of near infrared radiation", WO 98/22146; Kai Licha, et al. "In-vivo diagnostic process by near infrared radiation", WO 96/17628; Robert A. Snow, et al., Compounds, WO 98/48838).

In certain preferred embodiments, the fluorescent contrast agent is represented by the formula:

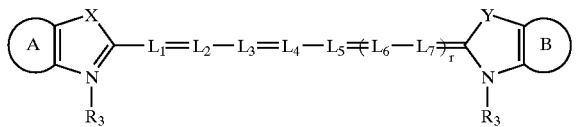

wherein $R_3$, independently for each occurrence, is a substituted or unsubstituted alkyl;

A and B are each, independently, 5–7 membered substituted or unsubstituted aromatic rings;

$L_1$–$L_7$ are each, independently, a substituted or unsubstituted methine, provided that one of $L_1$–$L_7$ is substituted with the linker group (R, defined above) which is attached to the bisphosphonate;

X and Y are the same or different and each is a group of the formula —O—, —S—, —CH=CH— or —C($R_4$)$_2$—;

$R_4$, independently for each occurrence, is a hydrogen or substituted or unsubstituted alkyl; and r is 0, 1 or 2.

Exemplary fluorescent contrast agents of this nature are described, for example, in PCT publication WO00/16810. In certain preferred embodiments, the fluorescent contrast agent is characterized by one or more of the following features: (a) it is free of a carboxylic acid group in a molecule; (b) r is 1; (c) 4 or more sulfonic acid groups are contained in the molecule; (d) 10 or less sulfonic acid groups are contained in a molecule; (e) A and B are, independently, benzo or naphtho rings; and (f) X and Y are —C(CH$_3$)$_2$—.

In certain embodiments, any two of $L_1$–$L_7$ are substituted and form a ring. An example of such an embodiment is the fluorescent contrast agent represented by the formula [III]

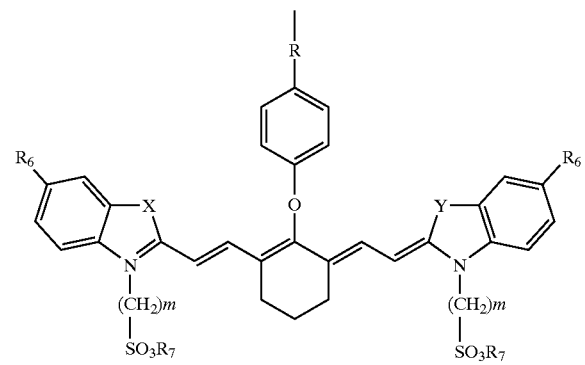

wherein

X and Y are as defined above, and preferably are each —C(CH$_3$)$_2$—;

$R_6$, independently for each occurrence, is hydrogen or —SO$_3$R$_7$;

$R_7$, independently for each occurrence, is hydrogen or a pharmaceutically acceptable counter ion, and is preferably sodium (NA);

m is 0, 1, 2, 3, 4 or 5, and is preferably 4.

Exemplary dyes of this nature are available commercially, such as from LI-COR, Inc. (Lincoln, Nebr.) and can be readily conjugated to a bisphosphonate moiety. For instance, the subject imaging agents can be derived through the use of IRDye80, IRDye78, IRDye38, IRDye40, IRDye41, IRDye700, or IRDye800 from LI-COR, Inc. (see also U.S. Pat. No. 6,027,709). These dyes include carbodiimide (CDI) active groups that can be covalently bonded to a biphosphonate moiety.

In comparison to other fluorophore/sensitizers, the photoproperties of sulphonated indocyanine derivatives such as IRDye78 (LiCor catalog number 829-05932) are optimal for in vivo use. Analysis has revealed peak absorption at 771 nm and peak emission at 796 nm for IRDye78, areas of the spectrum with the lowest possible tissue absorbance. IRDye78 has a high extinction coefficient (150,000 M$^{-1}$cm$^{-1}$) in aqueous medium, and a $\Phi_F$ of 34%. Finally, IRDye78 has been specifically designed for conjugation to other biomolecules.

As described in the appended examples, one preferred contrast agent is an amide linked conjugate of pamidronate and IRDye 78. Pamidronate is a primary amine-containing bisphosphonate, which can be coupled conveniently to NIR fluorophores. Pamidronate is conjugated to a near-infrared fluorophore. In preferred embodiments, the fluorophore is e.g., preferably one whose excitation maximum is about 771 nm and has an emission maximum is 796 nm, and extinction coefficient is 150,000 $M^{-1}cm^{-1}$ in aqueous environments. Purification of the product (Pam78) has been optimized by utilizing thin-layer chromatography. Pam78 binds to HA crystals with rapid kinetics, is competed with unconjugated pamidronate, and has a binding capacity consistent with previously published bisphosphonate conjugates.

C. Exemplary Formulations

Acute, sub-acute, and chronic administration of bisphosphonates has, in general, revealed little toxicity. This is generally explained by their rapid incorporation into calcified tissue and hence their short presence in the circulation. Accordingly, a wide variety of formulations and routes of administration are expected to be available for the subject contrast agents.

The compounds of the present invention can be administered to a mammalian host in a variety of forms adapted to the chosen route of administration, i.e., orally, or parentally. Parenteral administration in this respect includes, but is not limited to, administration by the following routes: intravenous, intramuscular, subcutaneous, intraocular, intrasynovial, transepithelially including transdermal, opthalmic, sublingual, and buccal; topically including opthalmic, dermal, ocular, rectal and nasal inhalation via insufflation and aerosol and rectal systemic.

The active compound may be orally administered, for example, when an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium sicarate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl, and propylparabens as a preservative, a dye and flavoring. Of course, any material used in preparing any dosage unit form should be pharmaceutically pure and substantially non-toxic in the amounts employed. In addition, the active compound maybe incorporated into sustained-release preparations and formulations. The active compound may also be administered parenterally or intraperitoneally. Solutions of the active compound as an ester, a free base or a pharmacologically acceptable salt can be prepared in water or other aqueous solution (e.g. water suitably mixed with a surfactant such as hydroxypropylcellulose). Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable, use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent of dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbicacid, thimersal, and the like. In many cases, it will be preferable to include isotonic agents, for example, sugars or sodium chloride. Prolonged absorption of the injectable compositions can be obtained by the use of agents delaying absorption, for example, aluminummonostearate and gelatin.

Sterile injectable solutions are prepared by incorporating the active compound in the required amount in the appropriate solvent with various of the other ingredients enumerated above, as required, typically followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

D. Exemplary Uses

The subject compositions can be used as part of an imaging technique to analyze bone and other tissue which may include hydroxyapatite.

An aspect of the invention is a method for evaluating a bone for its condition and biomechanical property. In certain embodiments, the subject contrast agents can be used as part of an in vivo imaging protocol for determining bone matrix density. In a particular embodiment, the invention contemplates measuring bone mineral density (BMD) of a selected region of bone in a small body portion of a human or other animal.

In this regard, the subject method can be used for example, to detect changes in bone matrix volume which correspond to the condition of the bone.

Thus, the invention provides a method for diagnosing osteoporosis which includes the use of the subject contrast agents. In this approach, a measure of trabecular thickness and bone perimeter, determined from bone images can be used together to assess the condition of trabecular bone at the site of interest.

In other embodiments, the subject contrast agents and imaging materials can be used to determine the biomechanical properties of bone in vivo, wherein the biomechanical properties are reflected in a set of anisotropic elastic constants, bone strength, or fracture risk.

Still another embodiment of the subject method is for diagnostic detection of bone diseases accompanied with abnormality of calcium hydroxyapatite, such as metastasis of cancer to bone, especially at the initial stage.

This invention provides imaging methods for use in an animal, which includes, but is not limited to, humans and other mammals. The term "mammals" or "mammalian subject" also includes farm animals, such as cows, hogs and sheep, as well as pet or sport animals such as horses, dogs and cats.

III. Exemplification

As described further below, NIR fluorescent bisphosphonate derivatives were synthesized and demonstrated to have nearly ideal optical and HA binding properties. Using this compound, what is believed to be the first NIR fluorescence imaging of a complete body system, the growing skeleton, in a living animal was obtained. In the same animal, NIR fluorescence imaging was compared to $^{99m}$Tc-MDP radioscintigraphy and magnetic resonance imaging.

A. Conjugation and Purification of a Near-infrared Fluorescent Small Molecule Ligand with Specific Binding to Hydroxyapatite The small molecule pamidronate (FIG. 1A, molecule I), which has specific binding to HA, was chosen as the bisphosphonate for this study since it has a single primary amine for conjugation and is readily available in powder form. It also has one of the shortest spacing elements (two carbons) between the HA binding portion of the molecule and the site of conjugation, hence providing a stringent test for the concept of using primary amine-containing bisphosphonates as ligands to which bulky NIR fluorophores can be attached.

Figure 1B:
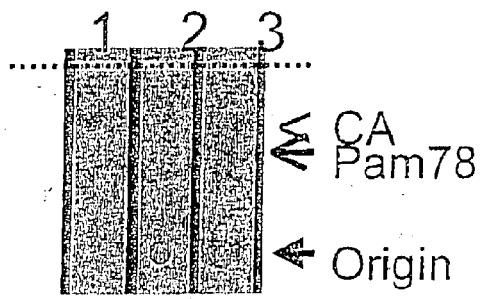

Covalent conjugation to the N-hydroxysuccinimide (NHS) ester of the NIR fluorophore IRDye78 (LI-COR, Lincoln, Nebr.; FIG. 1A, molecule II) was accomplished in one step as detailed in the Experimental Protocol. The resultant product, termed Pam78 (FIG. 1A, molecule III), was purified using thin-layer chromatography (TLC; FIG. 1B) and confirmed by mass spectroscopy (data not shown). Due to pamidronate's extreme insolubility in organic solvents, and IRDye78's base lability, the conjugation reaction had to be performed under near-neutral aqueous conditions. Despite this, we were able to achieve Pam78 yields of 18–21%.

B. Spectral Properties of IRDye78 and Pam78

Figure 1C:
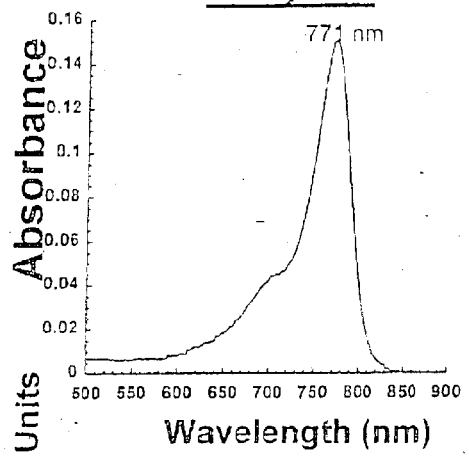
Figure 1C:
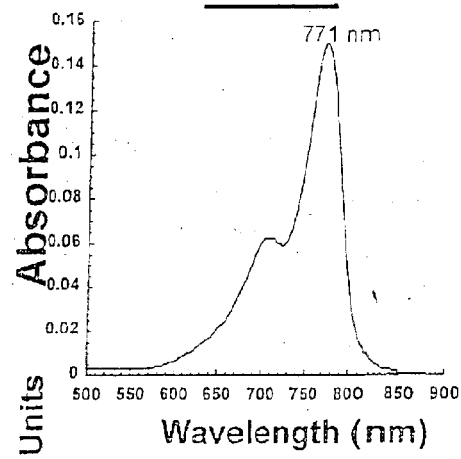
Figure 1D:
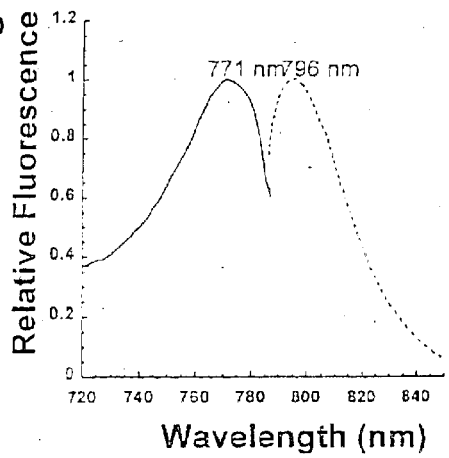
Figure 1D:
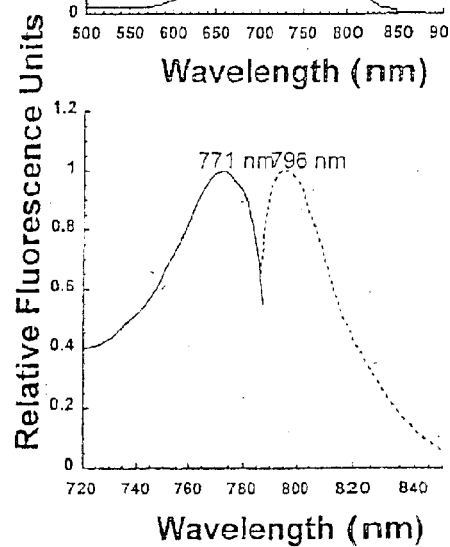

Absorbance wavelength scans of IRDye78 (FIG. 1C, left panel) and Pam78 (FIG. 1C, right panel) were performed as described in the Experimental Protocol. IRDye78 had a peak absorption at 771 nm, with a minor peak at 708 nm (discussed below). Peak absorption of Pam78 was unchanged from IRDye78, although the 708 nm peak was significantly more pronounced. Emission fluorescence scans (FIG. 1D, dashed lines), with excitation wavelength fixed at 771 nm, were performed. Both IRDye78 (FIG. 1D, left panel) and Pam78 (FIG. 1D, right panel) had a peak emission at 796 nm. Of note, excitation at the minor absorption peak of 708 nm resulted in identical peak emission wavelengths for both IRDye78 and Pam78 (data not shown), suggesting that this minor absorption peak is an alternative resonance structure and not an impurity in the preparation. Conjugation to pamidronate likely stabilizes this alternative resonance (compare FIG. 1C, left panel to right panel).

C. In Vitro Hydroxyapatite-binding Properties of IRDye78 and Pam78

Figure 2A:
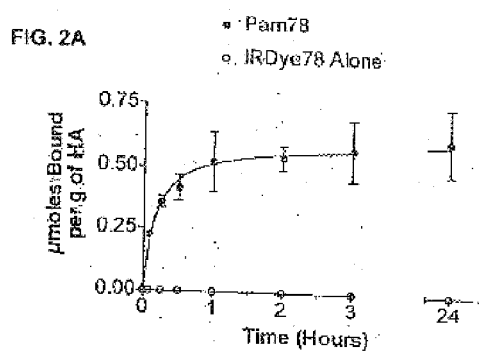

Bisphosphonates bind HA rapidly and with high specificity [4]. To determine whether pamidronate has bulk tolerance for relatively large molecules such as IRDye78, we performed a kinetic binding assay (FIG. 2A). Pam78 exhibited rapid binding to HA, with 37% of peak binding achieved in just five minutes and asymptotic binding by 1 hour. Continued binding to HA was seen even at the longest time point (24 hours) consistent with previously published results [4]. The carboxylic acid of IRDye78 (FIG. 2A) exhibited no detectable binding to HA during 24 hours of incubation.

Figure 2B:
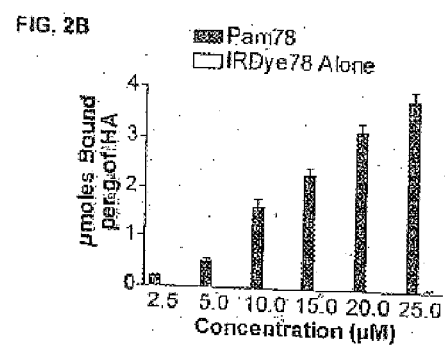

As observed previously, HA has an extremely high, and essentially unsaturable capacity for bisphosphonates, precluding measurement of an equilibrium binding constant [4]. However, we sought to determine if the capacity of HA to bind pamidronate was altered by conjugation to IRDye78. FIG. 2B shows the results of such an experiment. The measured binding capacity, plotted as a function of applied bisphosphonate concentration, was lower than previously published results for similar, but unconjugated, bisphosphonates [4] by a ratio exactly equal to the ratio of their respective molecular weights. This suggests that binding to HA was unaltered by conjugation, but the total capacity of binding was lowered by steric hindrance. Consistent with the experiment shown in FIG. 2A, IRDye78 alone exhibited no binding to HA.

Figure 2C:
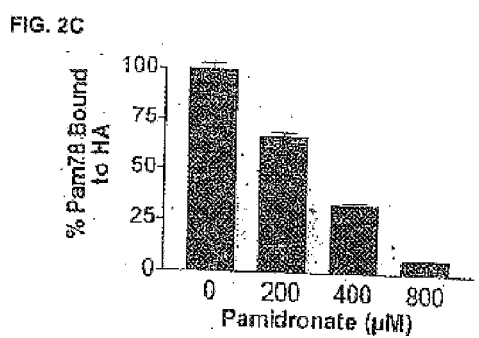
Figure 2D:
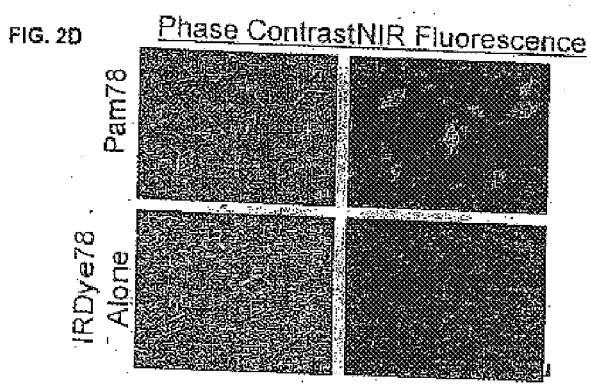

Designed as pyrophosphate-mimetics, bisphosphonates have extremely high specificity for hydroxyapatite both in vitro [4] and in vivo [20]. Nevertheless, we sought to confirm that Pam78 binding to hydroxyapatite could be competed by unlabeled pamidronate. FIG. 2C shows the results of such a competition experiment in which 2.5 $\mu$M Pam78 was bound to 1.5 mg/ml (1.5 mM) HA crystals in the presence of increasing concentrations of unlabeled pamidronate. Theoretical estimates suggest that HA has a maximum binding capacity of approximately $8.4 \times 10^{-4}$ moles pamidronate per gram HA. Hence, the HA in each 100 $\mu$l reaction would be expected to have a capacity of 126 nmol of pamidronate. As shown in FIG. 2C, Pam78 was effectively competed by increasing concentrations of unlabeled pamidronate, with 90% inhibition seen in the presence of 80 nmol (800 $\mu$M) unlabeled pamidronate.

D. In Vivo Near-infrared Fluorescence Imaging of HA Using IRDye78 and Pam78

The small animal imaging system described in the Experimental Protocol is similar to one published previously [21]. It has an adjustable circular field of view (FOV) with a theoretical and measured resolution, respectively, of 100$\mu$ and 200$\mu$ at a of FOV diameter of 10 cm, and 10$\mu$ and 25$\mu$ at a FOV diameter of 1 cm. Fluorescence excitation power density of the system was 18 mW/cm$^2$, with minimal spatial variation. Zoom lens and camera were chosen for excellent transmission and sensitivity, respectively, at 800 nm.

In preliminary experiments, it was determined that body hair causes significant NIR light scatter and essentially precludes planar NIR imaging of small animals (see also below). Hence, hairless (nu/nu) mice were used throughout this study. FIGS. 3A–F show a typical experiment using the carboxylic acid of IRDye78 injected intravenously. Autofluorescence of the animal using an excitation band of 750±25 nm and emission band of 810±20 nm was negligible (FIGS. 3A–L). Within one minute, and appearing relatively stable for the next fifteen minutes, the entire mouse became fluorescent (FIGS. 3A–F). Of note, any small defects present on the animal's skin became pronounced after IRDye78 injection (FIGS. 3A–F; discussed below). Over the ensuing six hours, IRDye78 was eliminated rapidly by the genitourinary and biliary systems (FIGS. 3D, F). Gallbladder filling and contraction, and intestinal peristalsis were easily visible during this time (data not shown). By six hours, NIR fluorescence had returned to near background except in the above sites of elimination (FIGS. 3D, F).

Intravenous injection of Pam78 (FIGS. 3G–L) resulted in similarly rapid distribution throughout the body and intense NIR fluorescence of the animal. However, as Pam78 was cleared by the genitourinary and biliary systems, areas of exposed HA became visible. As early as 15 minutes post-injection, Pam78 uptake in the spine, ribs, paws and knees could be detected above background, and by three hours, most bony structures were visible (FIGS. 3G–L). Although a 500 msec exposure time was used throughout this study to match the full dynamic range of the camera, acquisition times as short as 50 msec resulted in excellent quality images, which suggests that real-time dynamic NIR fluorescence imaging will be possible with newly introduced interlined NIR cameras.

E. Pharmacokinetics and Percentage Uptake of IRDye78 and Pam78

Although the fluorescent signal from the entire animal could be followed over time, we sought to quantitate the rate of plasma elimination of IRDye78 and Pam78 after intravenous injection. The data (FIG. 3M) suggest that IRDye78 achieves peak concentrations within 1 minute after injection and exhibits a two-phase elimination from the plasma, with early and late half-lives of 7.2 and 24.7 minutes, respectively. The late in vivo half-life is consistent with the late in vivo half-lives reported for similar poly-sulphonated indocyanine NIR fluorophores [22]. Pam78 (FIG. 3N) also shows peak plasma concentration by 1 minute, with a more rapid clearance having early and late half-lives of 5.0 and 15.4 minutes, respectively. This is not surprising given the rapid in vivo binding of Pam78 to HA simultaneous with its elimination by the genitourinary and biliary systems, F. Comparasion of Near-infrared Fluorescence Imaging to $^{99m}$Tc-MDP Radiocintigraphy Six hours after Pam78 injection, fluorescent background was such that optimal images were obtained. All of the dorsal bony structures delineated in FIGS. 3G–L became better defined, and ventral imaging revealed additional structures such as bones of the maxilla, sternum and knees.

Prior to this study, the gold standard for imaging of HA was a bone scan with $^{99m}$Tc-MDP. To compare, directly, these two imaging methods, the same animal was re-injected with $^{99m}$Tc-MDP and imaged by planar radioscintigraphy six hours later. Due to the inherent tradeoff between pinhole size and FOV, it was not possible to image the entire animal with higher resolution than that shown. Also, the radioscintigraphic image required a 30 minute integration time for 0.4 mCi of $^{99m}$Tc-MDP injected versus a 500 msec image acquisition time for NIR fluorescence using 2.6 nmol of Pam78.

G. Target Depth and Effects of Scatter on Signal Intensity and Image Quality Using Near-infrared Fluorescent Ligands The correlation of anatomical landmarks imaged by MRI with NIR signal intensity permits the modeling of observed NIR fluorescence signal as a function of target depth beneath the skin surface. The net NIR fluorescent signal intensities of the first seven visible spinous processes were plotted against their depth beneath the surface of the skin as measured by MRI. The data fit an exponential decay curve where measured intensity is proportional to $e^{-kd}$, $k=-0.43$/mm and d=distance from the skin surface to the target in millimeters ($R_2$ of fit=0.98). The significance of this model is discussed below.

H. Quantitation of Pam78 Skeletal Uptake

To quantitate percentage uptake of injected dose, we first tried to isolate Pam78 directly from excised bones. Unfortunately, the harsh conditions necessary for bone dissolution (6 N HCl) destroyed the fluorophore (data not shown). However, we were able to estimate skeletal uptake by measuring fluorescence intensity of the ribs in the skinless animal. Calibration standards matching the geometry of the ribs were placed next to the animal and mean fluorescence intensities of each standard and the caudal three ribs on each side were measured. Pam78 concentration (mean±S.E.M.) was found to be $0.91\pm0.027$ $\mu$M. Assuming a bone density of 1.8 g/cm$^3$ [23] and a skeletal weight of 11.8% body weight [24], 1.5 nmol (57%), out of 2.6 nmol injected, bound to the skeleton. The skeletal uptake of Pam78 compares favorably with the 52% uptake reported in rats using $^{99m}$Tc-MDP [25].

I. High-resolution In Vivo Near-infrared Fluorescence Imaging of HA in Specific Anatomic Sites The small animal NIR fluorescence imaging system described above was designed to include zoom capability. Six hours after Pam78 injection, the same animal shown in FIGS. 3G–L was used to obtain high-resolution images of various sites of exposed HA (FIGS. 4A–E). Although scatter from the skin and overlying soft tissue resulted in blurring of some structures, most bones of the animal could be visualized and some, like the bones of the maxilla, could be seen with extremely high clarity (discussed below).

J. Discussion of Results

This study highlights many of the principles of NIR fluorescence imaging. Of paramount importance is the choice of fluorophore. The NIR window has a local minimum at approximately 800 nm, and fluorophores with excitation/emission wavelengths close to 800 nm should permit maximal photon penetration into living tissue. IRDye78 and its derivatives have an excitation wavelength of 771 nm, emission wavelength of 796 nm, and a relatively high extinction coefficient and quantum efficiency. The NHS ester of IRDye78 permits one-step conjugation to primary-amine-containing ligands, and products are easily purified using low cost TLC. Poly-sulphonated indocyanines such as IRDye78 have extremely low toxicities, and plasma half-lives in the range of 10–30 minutes result in rapid clearance of background signal. Pam78 also appears to be stable in vivo since even twelve hours post-injection there is no degradation of skeletal signal (data not shown). This suggests that the amide bond between pamidronate and IRDye78, and the fluorophore itself, were not hydrolyzed significantly.

Pam78 provides a convenient reagent for creating "embedded targets" in a living animal. NIR fluorescence imaging systems are usually evaluated using fluorescent phantoms that seldom have relevance to in vivo imaging. Pam78, however, creates an essentially infinite number of target structures embedded at all depths within a living animal. Such a reagent should be extremely valuable for creating the much needed next generation of NIR fluorescence imaging systems.

By measuring the observed NIR fluorescence intensity as a function of optical path length between excitation light and target, we were able to derive the exponential decay constant of $k=-0.43$/mm. This model predicts that the presence of skin (0.89 mm thick on the back of a 25 g nude mouse; AZ and JVF, unpublished observations) would reduce net NIR fluorescence signal intensity by 32%. After adjusting for exposure time, comparison of the animal with and without skin resulted in an intensity attenuation of 44%, in reasonable agreement with the model. This model may be useful as a frame of reference for investigators contemplating the use of NIR fluorescence for target detection in vivo. Of course, the presence of skin markedly reduces the quality of the image due to scatter. Optical scatter is a major limitation to planar imaging using NIR light. The use of an optical coupling medium and/or tomographic imaging may provide a means of minimizing this effect.

Pam78 has several immediate applications in the study of skeletal disease. It provides high resolution imaging of HA without compromising sensitivity and specificity FIG. 3G–L, 4A–E). Certain structures such as the bones of the maxilla (FIG. 4A) are seen with near-photographic clarity, which should permit detailed, non-invasive study of maxillofacial development. Skeletal development in higher and lower vertebrates, as well as animal models of bony disease, could be studied with this technology. Although the present study was conducted with hairless animals, chemical hair removal using commercially available products should permit any mouse strain to be used (AZ and JVF; unpublished obseivations).

Pathologic skeletal processes such as osteoblastic metastases should also be readily detectable using this technology. Presently, the gold standard for imaging exposed HA is radioscintigraphy with $^{99m}$Tc-MDP. To compare directly NIR fluorescence imaging with radioscintigraphy, we developed a procedure by which the same animal was imaged sequentially with both modalities. In addition, the same animal was imaged with high field magnetic resonance imaging so that all results could be cross-correlated to the precise location of anatomical landmarks. As one might expect, there were distinct advantages to each method. NTR fluorescence imaging was extremely rapid (500 msec or less for complete image acquisition and processing), had high sensitivity after only 2.6 nmol of injected Pam78, and offered relatively high spatial resolution (FIGS. 4A–E). However, deep structures were either poorly visualized or not visualized at all with our experimental apparatus due to skin and soft tissue attenuation and scatter. In comparison, planar radioscintigraphy required long integration times, and a tradeoff between FOV and spatial resolution. However, imaging of deep structures was possible since the 140 keV γ-ray is highly penetrant and minimally scattered. We propose that NIR fluorescence detection may permit the earliest genetic changes associated with osteoblastic metastases to be studied more easily in mouse model systems since small lesions can be detected rapidly, with high resolution, and non-isotopically in the living animal.

The technology described in this study may also have several non-skeletal applications. First, the carboxylic acid of IRDye78 distributes rapidly throughout the body and is able to highlight even small defects in the skin (FIGS. 3A–F). It may be possible, therefore to use IRDye78 as a part of a sensitive detection system for dermatologic disease. Indeed, a related NIR fluorophore, indocyanine green, has already been used in such a manner. Second, there are several effects of pamidronate, such as direct osteoclast inhibition and parasite toxicity, that defy mechanistic explanation at present. Pam78 may be a valuable reagent to visualize the binding of pamidronate to osteoclasts and parasites in the hope of better defining its mechanism of action. Third, middle/inner ear anomalies caused by hydroxyapatite deposition, such as otosclerosis, could be detected with high sensitivity and specificity by injecting Pam78 intravenously, placing a fiberscope against the tympanic membrane, and directly visualizing NIR fluorcscence.

Finally, perhaps one of the most exciting applications of this technology will be in imaging the earliest manifestations of coronary calcification. Even $^{99m}$Tc-MDP is capable of imaging aortic calcification, but only in advanced disease and with low resolution. Intravenous or intracoronary injection of Pam78 would be expected to highlight even microscopic HA deposits, since intimal thickness is well within the range of this technology. Analogous to intravascular ultrasound, a NIR fluorescence angioscope inserted into a coronary artery should permit visualization of the earliest precursor lesions of vascular calcification and, hence, permit intervention before a conventional plaque forms. Indeed, if it is determined that the yield of triplet formation of Pam78 is sufficient, it may be possible to perform both detection (via fluorescence angioscopy) and treatment (via photodynamic therapy) of sub-clinical atherosclerotic lesions with this single compound.

K. Experimental Protocol

Reagents. Pamidronate disodium was a generous gift from Interchem Corporation (Paramus, N.J.). The NHS ester of IRDye78™ was purchased from LI-COR (Lincoln, Nebr.) and stored under nitrogen at −80° C. until use. Immediately before conjugation, it was resuspended in DMSO to 22.8 mM. The carboxylic acid of IRDye78 was a generous gift from LI-COR (Lincoln, Nebr.). Hydroxyapatite (CAS# 1306-06-5; MW 1004.6) was purchased from Calbiochem (La Jolla, Calif.; Catalog# 391947). Fluoromount-G was purchased from Southern Biotechnology Associates, Inc. (Birmingham, Ala.). All other chemicals were purchased from Sigma (St. Louis, Mo.). $H_2O$ used in this study was purified to 18 MΩ on a Milli-Q apparatus (Millipore, Bedford, Mass.).

Conjugation and Purification of Pam78. All steps were performed under reduced light conditions. 42.5 mM pamidronate in $H_2O$ was adjusted with 0.1 N NaOH to pH 8.5. In a 1 ml reaction were mixed 10 mM pamidronate and 5.5 mM IRDye78 NHS ester, with the remainder of the volume $H_2O$. The reaction proceeded 18 hours at room temperature with constant motion. Reaction components were separated on a 60 Å pore size normal phase thin-layer chromatography plate (Whatman LK6DF), without spotting on the preabsorbent layer. Mobile phase was 65% acetonitrile and 35% $H_2O$. IRDye78 and its products are bright green and are followed easily during purification. For analytic preparations, unconjugated pamidronate was visualized by spraying the TLC plate with 0.25% ninhydrin in acetone and heating. The desired product band was scraped with a razor blade, and the silica fragments were placed in a 15 ml polypropylene tube. After elution with 20% acetonitrile and 80% $H_2O$, silica fragments were removed by passage through a $0.2\mu$ Durapore PVDF Ultrafree-MC membrane filter (Model UFC3-0GV-25, Millipore, Bedford, Mass.). After lyophilization, the final product was resuspended in $H_2O$, re-filtered as above, and stored in the dark at −80° C. until use. Concentration of the final product and yield were calculated by measuring the absorbance at 771 nm, using an extinction coefficient of $\epsilon=150,000$ $M^{-1}cm^{-1}$.

Spectral Measurements. Absorbance measurements and scans were performed on a Model DU-600 spectrophotometer (Beckman, Fullerton, Calif.) using 1 $\mu$M of each compound in 20 mM N-ethylmorpholine (NEM), pH 7.4 and 150 mM KCl (NK buffer). Fluorescence measurements, and excitation/emission scans were performed on a SPECTRAmax Gemini XS microplate reader (Molecular Devices, Sunnyvale, Calif.) using Model 655076 black 96-well plates (Greiner, Lake Mary, Fla.), and 500 mM of each compound in NK buffer. Curves were analyzed using SOFTmax PRO software (Molecular Devices, Sunnyvale, Calif.) and plotted using Prism3 for the Macintosh (GraphPad Software, Inc., San Diego, Calif.).

In Vitro Hydroxyapatite Binding Experiments. For kinetic measurements of binding to HA, 5 $\mu$M Pam78 or the carboxylic acid of IRDye78 was added from a 20x stock solution to 100 $\mu$l NK buffer containing 1.5 mg/ml (1.5 mM) HA. Suspensions were continuously vortexed at 37° C. for the time indicated. Bound and unbound material was separated using a 0.2 µm filter in a 96-well format (Model MAGVN2210, Millipore, Bedford, Mass.), and the concentration of material in the filtrate was measured using the SPECTRAmax Gemini XS fluorescence microplate reader set for an excitation wavelength of 771 nm and an emission wavelength of 796 nm. Bound material was calculated by subtracting unbound compound from the total added to each reaction.

For measurement of steady-state binding to HA, the indicated concentration of Pam78 or the carboxylic acid of IRDye78 was added from a 20× stock solution to 100 µl NK buffer containing 1.5 mg/ml (1.5 mM) HA. Suspensions were continuously vortexed at 37° C. for three hours and processed as described for kinetic experiments.

For competition experiments, free pamidronate was pre-incubated in 100 µl NK buffer with 1.5 mg/ml (1.5 mM) HA for five minutes at room temperature with continuous vortexing. Pam78 was then added from a 20× stock solution to a final concentration of 2.5 µM. Incubation at 37° C. with continuous vortexing continued for three hours prior to filtration and measurement as described above.

For NIR fluorescence imaging of HA crystals, 1 µM of Pam78 or the carboxylic acid of IRDye78 in 100 µl NK buffer was incubated with 1.5 mg/ml (1.5 mM) HA for fifteen minutes at room temperature with continuous vortexing. Crystals were washed 3× with NK buffer, resuspended in Fluoromount-G, and mounted on glass slides.

Near-ifrrared Fluorescence Microscopy. NIR fluorescence images were acquired on a Nikon Eclipse TE-300 epi-fluorescence microscope equipped with a 100W Mercury light source, NIR compatible optics, and a NIR-compatible 10× PlanFluor objective lens (Model 93171, Nikon, Melville, N.Y.). A custom IRDye78 filter set (Chroma Technology Corporation, Brattleboro, Vt.) was comprised of a 750±25 nm excitation filter, a 785 nm dichroic mirror, and an 810±20 nm emission filter. Images were acquired on a Photometrics Sensys CCD Camera (Model 1401, Roper Scientific, Tucson, Ariz.) with heat filter removed. Image acquisition and analysis was performed using IPLab software (Scanalytics, Fairfax, Va.).

Small Animal In Vivo Near-ifrrared Fluorescence Imaging System. The system was constructed on an anti-vibration table (Technical Manufacturing Corporation, Peabody, Mass.) and consisted of two 150 W halogen light sources (Model PL-900, Dolan-Jenner, Lawrence, Mass.) to which were mounted light guides (Model BXS-236) and 750±25 nm excitation filters (Chroma Technology Corporation, Brattleboro, Vt.). Emitted light passed through an 810±20 nm emission filter (Chroma Technology Corporation, Brattleboro, Vt.) and was collected using a Macrovideo zoom lens with detachable close-up lens (Optem Avimo Precision Instruments, Fairport, N.Y.), into the above Photometrics Sensys CCD Camera. Image acquisition was controlled using IPLab software and typically consisted of a 250 to 500 msec acquisition time using a camera gain of 2. Excitation power density was measured using a calibrated thermopile detector (Model 2M) and 1000 V/V pre-amplifier (Model 1010; both from Laser Components, Santa Rosa, Calif.).

Compound Injection and Measurement of Serum Concentration. Hairless 7 week old male nu/nu mice (Charles River Laboratories, Wilmington, Mass.; average weight 25 g) were anesthetized with 50 mg/kg i.p. pentobarbital. The lateral tail vein was visualized using a flashlight and 2.6 nmol of compound resuspended in 80 µl of phosphate buffered saline (PBS) was injected using a bent, 30 gauge, ½" needle. For measurement of plasma concentration, the tip of the tail of an anesthetized animal was cut with a razor blade, and 75 µl of whole blood was milked, and collected with a capillary tube. After clotting and removal of cells by centrifugation, serum was diluted 1:10 in 50 mM Hepes, pH 7.4 and a wavelength scan from 400 nm to 850 nm was performed. Serum concentration was determined by peak height at 771 nm after subtraction of background (pre-injection serum), and correction for hemoglobin absorbance.

Magnetic Resonance Imaging (MRI). Animals were anesthetized with 50 mg/kg i.p. pentobarbital, placed in a custom low-pass birdcage coil (10 cm length, 6 cm diameter), and imaged with a 3T whole body scanner (General Electric Medical Systems, Waukesha, Wis.). Images were acquired with an 8 cm FOV using a 3D fast gradient echo sequence. Other parameters included a 256×256 pixel matrix size, slice thickness of 0.7 mm, TE=2.6 msec, TR=10.2 msec, and flip angle=15°.

Planar $^{99m}$Techetium-MDP Radioscintigraphy. Anesthetized animals were injected with 0.4 mCi $^{99m}$Tc-MDP and imaged six hours later. Dorsal images in a 512×512 pixel format were integrated for a total of 30 minutes via a custom 1 mm tantalum pinhole mounted on a Forte gamma camera (ADAC Laboratories, Milpitas, Calif.).

L. References

1. Marks, S. C., Jr. & Popoff, S. N. Bone cell biology: the regulation of development, structure, and function in the skeleton. *Am. J. Anat.* 183, 1–44 (1988).

2. Jakoby, M. G. & Semenkovich, C. F. The role of osteoprogenitors in vascular calcification. *Curr. Opin. Nephrol. Hypertens.* 9, 11–15 (2000).

3. Watson, K. E. Pathophysiology of coronary calcification. *J. Cardiovasc. Risk* 7, 93–97 (2000).

4. Jung, A., Bisaz, S. & Fleisch, H. The binding of pyrophosphate and two bisphosphonates by hydroxyapatite crystals. *Calcif Tissue Res.* 11, 269–280 (1973).

5. Fleisch, H. Bisphosphonates—history and experimental basis. *Bone* 8 Suppl 1, S23–28 (1987).

6. Altkorn, D. & Vokes, T. Treatment of postmenopausal osteoporosis. *JAMA* 285, 1415–1418 (2001).

7. Eastell, R. Treatment of postmenopausal osteoporosis. *N. Engl. J. Med.* 338, 736–746 (1998).

8. Glorieux, F. H., et al. Cyclic administration of pamidronate in children with severe osteogenesis imperfecta. *N. Engl. J. Med.* 339, 947–952 (1998).

9. Mundy, G. R. & Yoneda, T. Bisphosphonates as anti-cancer drugs. *N. Engl. J. Med.* 339, 398–400 (1998).

10. Klenner, T., Wingen, F., Keppler, B. K., Krempien, B. & Schmahl, D. Anticancer-agent-linked phosphonates with antiosteolytic and antineoplastic properties: a promising perspective in the treatment of bone-related malignancies? *J. Cancer Res. Clin. Oncol.* 116, 341–350 (1990).

11. Fujisaki, J., et al. Osteotropic drug delivery system (ODDS) based on bisphosphonic prodrug. I: synthesis and in vivo characterization of osteotropic carboxyfluorescein. *J. Drug Target.* 3, 273–282 (1995).

12. Fujisaki, J., et al. Physicochemical characterization of bisphosphonic carboxyfluorescein for osteotropic drug delivery. *J. Pharm. Pharmacol.* 48, 798–800 (1996).

13. Fujisaki, J., et al. Osteotropic drug delivery system (ODDS) based on bisphosphonic prodrug. III: Pharmacokinetics and targeting characteristics of osteotropic carboxyfluorescein. *J. Drug Target.* 4, 117–123 (1996).

14. Fujisaki, J., et al. Osteotropic drug delivery system (ODDS) based on bisphosphonic prodrug. V. Biological disposition and targeting characteristics of osteotropic estradiol. *Biol. Pharm. Bull.* 20, 1183–1187 (1997).

15. Fujisaki, J., et al. Osteotropic drug delivery system (ODDS) based on bisphosphonic prodrug. I.v. effects of osteotropic estradiol on bone mineral density and uterine weight in ovariectomized rats. *J. Drug Target.* 5, 129–138 (1998).

16. Hirabayashi, H., et al. Bone-specific delivery and sustained release of diclofenac, a non-steroidal anti-inflammatory drug, via bisphosphonic prodrug based on the Osteotropic Drug Delivery System (ODDS). *J. Control. Release* 70, 183–191 (2001).

17. Bachman, C. H. & Ellis, E. H. Fluorescence of bone. *Nature* 206, 1328–1331 (1965).

18. Prentice, A. I. Autofluorescence of bone tissues. *J. Clin. Pathol.* 20, 717–719 (1967).

19. Chance, B. Near-infrared images using continuous, phase-modulated, and pulsed light with quantitation of blood and blood oxygenation. *Ann. N.Y. Acad. Sci.* 838, 29–45 (1998).

20. Lin, J. H., Duggan, D. E., Chen, I. W. & Ellsworth, R. L. Physiological disposition of alendronate, a potent anti-osteolytic bisphosphonate, in laboratory animals. *Drug Metab Dispos* 19, 926–32 (1991).

21. Mahmood, U., Tung, C. H., Bogdanov, A., Jr. & Weissleder, R. Near-infrared optical imaging of protease activity for tumor detection. *Radiology* 213, 866–870 (1999).

22. Miwa, N., et al. Near-infrared fluorescent contrast agent and fluorescence imaging. Patent Cooperation Treaty WO 00/16810 (2000).

23. Reilly, D. T. & Burstein, A. H. The elastic and ultimate properties of compact bone tissue. *J. Biomech.* 8, 393–405 (1975).

24. McKern, N. M. Comparison of skeletal growth in normal and "little" mice. *Growth* 46, 53–59 (1982).

25. Cleynhens, B., et al. $^{99m}$Tc-bone agents with rapid renal excretion, in *Technetium, rhenium and other metals in chemistry and nuclear medicine*, Nicolini, M. & Mazzi, U., Eds. Servizi Grafici Editoriali: Padova. p. 611–614 (1999).

26. Quaresima, V., Matcher, S. J. & Ferrari, M. Identification and quantification of intrinsic optical contrast for near-infrared mammography. *Photochem. Photobiol.* 67, 4–14 (1998).

27. Farkas, D. L., et al. Non-invasive image acquisition and advanced processing in optical bioimaging. *Comput. Med. Imaging Graph.* 22, 89–102 (1998).

28. Ntziachristos, V., Yodh, A. G., Schnall, M. & Chance, B. Concurrent MRI and diffuse optical tomography of breast after indocyanine green enhancement. *Proc. Natl. Acad. Sci. U.S.A.* 97, 2767–2772 (2000).

29. Sabatakos, G., et al. Overexpression of DeltaFosB transcription factor(s) increases bone formation and inhibits adipogenesis. *Nat. Med.* 6, 985–990 (2000).

30. Olsen, B. R., Reginato, A. M. & Wang, W. Bone development. *Annu. Rev. Cell. Dev. Biol.* 16, 191–220 (2000).

31. Gunther, T. & Schinke, T. Mouse genetics have uncovered new paradigms in bone biology. *Trends Endocrinol. Metab.* 11, 189–193 (2000).

32. Drake, W. M., Kendler, D. L. & Brown, J. P. Consensus statement on the modern therapy of Paget's disease of bone from a Western Osteoporosis Alliance symposium. *Clin. Ther.* 23, 620–626 (2001).

33. Karrer, S., et al. Photochemotherapy with indocyanine green in cutaneous metastases of rectal carcinoma *Dtsch. Med. Wochenschr.* 122, 1111–1114 (1997).

34. Abels, C., et al. Indocyanine green (ICG) and laser irradiation induce photooxidation. *Arch. Dermatol. Res.* 292, 404–411 (2000).

35. Rogers, M. J., et al. Cellular and molecular mechanisms of action of bisphosphonates. *Cancer* 88, 2961–2978 (2000).

36. Martin, M. B., et al. Bisphosphonates inhibit the growth of *Trypanosoma brucei, Trypanosoma cruzi, Leishmania donovani, Toxoplasma gondii,* and *Plasmodium falciparum*: a potential route to chemotherapy. *J. Med. Chem.* 44, 909–916 (2001).

37. Lim, D. J. & Saunders, W. H. Otosclerotic stapes: morphological and microchemical correlates. An electron microscopic and x-ray analytical investigation. *Ann. Otol. Rhinol. Laryngol.* 86, 525–540 (1977).

38. Ikehira, H., Furuichi, Y., Kinjo, M., Yamamoto, Y. & Aoki, T. Multiple extra-bone accumulations of technetium-99m-HMDP. *J. Nucl. Med. Technol.* 27, 41–42 (1999).

39. Dupouy, P., Geschwind, H. J., Pelle, G., Gallot, D. & Dubois-Rande, J. L. Assessment of coronary vasomotion by intracoronary ultrasound *Am Heart J* 126, 76–85 (1993).

40. Rockson, S. G., et al. Photoangioplasty for human peripheral atherosclerosis: results of a phase I trial of photodynamic therapy with motexafin lutetium (Antrin). *Circulation* 102, 2322–4 (2000).

What is claimed is:

1. A contrast agent represented in the general formula [I] or pharmaceutically acceptable salts thereof:

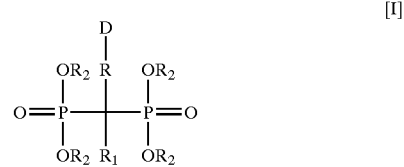

wherein

D represents a near infrared fluorescent moiety having excitation and emission spectra between about 650 nm and about 1000 nm;

R represents a linking group that covalently links the dye (D) and bisphosphonate moiety;

$R_1$ represents H, —OH, or a halogen; and $R_2$ represents, independently for each occurrence, a free electron pair, hydrogen, or a pharmaceutically acceptable counterion.

2. The agent of claim 1, wherein R is an amine substituted lower-alkyl which forms an amide bond with a pendant group of the fluorescent moiety.

3. The agent of claim 2, wherein R is —$(CH_2)_L$—NH—, where L is an integer from 1 to 6.

4. The agent of claim 1, wherein $R_1$ is —OH or —Cl.

5. The agent of claim 1, wherein D is a near-infrared fluorescent dye.

6. The agent of claim 5, wherein D is a polysulfonated indocyanine dye.

7. The agent of claim 1, wherein the fluorescent moiety is represented by the formula [II]:

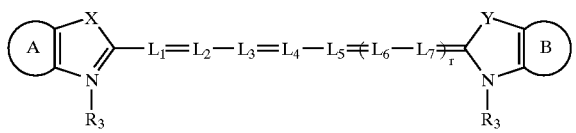

wherein $L_1$–$L_7$ are each, independently, a substituted or unsubstituted methine, provided that one of $L_1$–$L_7$ is substituted with the linker group R which is attached to the bisphosphonate;

$R_3$, independently for each occurrence, is a substituted or unsubstituted alkyl;

A and B are each, independently, 5–7 membered substituted or unsubstituted aromatic rings;

X and Y are the same or different and each is a group of the formula —O—, —S—, —CH=CH— or —C($R_4$)$_2$—;

$R_4$, independently for each occurrence, is a hydrogen or substituted or unsubstituted lower alkyl; and r is 0, 1 or 2.

8. The agent of claim 7, wherein the fluorescent moiety has one or more of the following features: (a) is free of a carboxylic acid group in a molecule; (b) r is 1; (c) includes 4 or more sulfonic acid groups; (d) includes 10 or less sulfonic acid groups; (e) A and B are, independently, benzo or naphtho rings; and (f) X and Y are —C(CH$_3$)$_2$—.

9. The agent of claim 1, wherein the fluorescent moiety is represented by the formula [III]

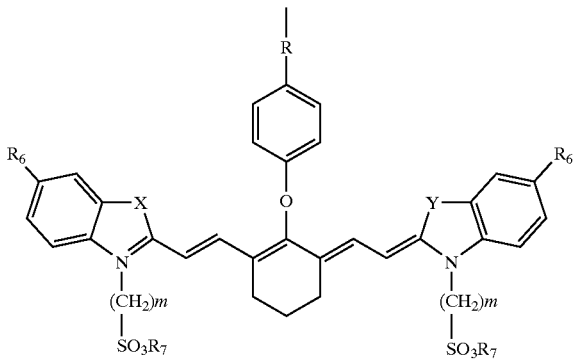

wherein

X and Y are the same or different and each is a group of the formula —O—, —S—, —CH=CH— or C($R_4$)$_2$—;

$R_4$, independently for each occurrence, is a hydrogen or substituted or unsubstituted lower alkyl; and $R_6$, independently for each occurrence, is hydrogen or —SO$_3$R$_7$;

$R_7$, independently for each occurrence, is hydrogen or a pharmaceutically acceptable counter ion;

m is 0, 1, 2, 3, 4 or 5.

10. The agent of claim 1, wherein the near-infrared fluorescent moiety has an extinction coefficient of at least 100,000 M$^{-1}$cm$^{-1}$ in aqueous medium.

11. The agent of claim 1, wherein the near-infrared fluorescent moiety has a quantum efficiency, $\Phi_F$, of at least 25%.

12. The agent of claim 1, having a half-life in the human body of at least 10 minutes.

13. A contrast agent comprising a bisphosphonate covalently linked to a near-infrared fluorescent moiety, wherein the contrast agent (a) has an extinction coefficient of at least 100,000 M$^{-1}$ cm$^{-1}$ in aqueous medium, and (b) has a half-life in the human body of at least 10 minutes.

14. The contrast agent of claim 13, wherein the bisphosphonate is selected from the group consisting of alendronate, clodronate, EB-1053, etidronate, ibandronate, incadronate, neridronate, olpadronate, phosphonate, pamidronate, risedronate, tiludronate, YH 529 and zoledronate.

15. A method for manufacturing a composition for in vivo imaging comprising formulating a contrast agent of claim 1 in a pharmaceutically acceptable excipient.

16. A kit for in vivo imaging comprising a contrast agent of claim 1 in association with instructions for administering the contrast agent to a patient.

17. A method for in vivo imaging of tissue with exposed hydroxyapatite, comprising, (i) administering to an animal a contrast agent of claim 1 in an amount sufficient to render hydroxyapatite-containing tissue detectable by a fluorescence detector;

(ii) obtaining a fluorescent image of the animal, or at least a portion thereof, at a wave length(s) which detects the contrast agent;

(iii) constructing an image of the animal including the pattern of distribution of the contrast agent.

18. The method of claim 17, for evaluating a bone for its condition and/or biomechanical property.

19. The method of claim 18, for determining bone matrix density.

20. The method of claim 18, for detecting changes in bone matrix volume.

21. The method of claim 18, as part of a protocol for diagnosing osteoporosis.

22. The method of claim 18, for determining at least one of anisotropic elastic constants, bone strength, or fracture risk.

23. The method of claim 17, for diagnostic detection of bone diseases accompanied with abnormality of calcium hydroxyapatite.

24. The method of claim 23, for detecting the presence of osteoblastic metastase.

25. The method of claim 17, for detecting of vessel micro-calcification.

26. The method of claim 17, wherein the animal is a human.

27. The agent of claim 7, wherein A and B are independently selected from the group consisting of benzo- and naptho-rings.

* * * * *